US00PP31882P3

(12) United States Plant Patent
Danziger

(10) Patent No.: US PP31,882 P3
(45) Date of Patent: Jun. 16, 2020

(54) ***IMPATIENS* PLANT NAMED 'DIMPSHABO'**

(50) Latin Name: *Impatiens hawkeri*
Varietal Denomination: DIMPSHABO

(71) Applicant: Gavriel Danziger, Beit Dagan (IL)
(72) Inventor: Gavriel Danziger, Beit Dagan (IL)
(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/602,187

(22) Filed: Aug. 22, 2019

(65) Prior Publication Data

US 2020/0068766 P1 Feb. 27, 2020

(51) Int. Cl.
*A01H 5/02* (2018.01)
*A01H 6/16* (2018.01)

(52) U.S. Cl.
USPC ..... Plt./318.1
CPC ..... *A01H 6/165* (2018.05)

(58) Field of Classification Search
USPC ..... Plt./318.1, 318.4, 318.5, 318.6
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Impatiens* plant named 'DIMPSHABO' is disclosed, characterized by well branched, sun resistant plants with large flowers. Flowers are uniquely colored violet flushed with purple. The new variety is an *Impatiens*, normally produced as an outdoor garden or container plant.

2 Drawing Sheets

Figure 1:
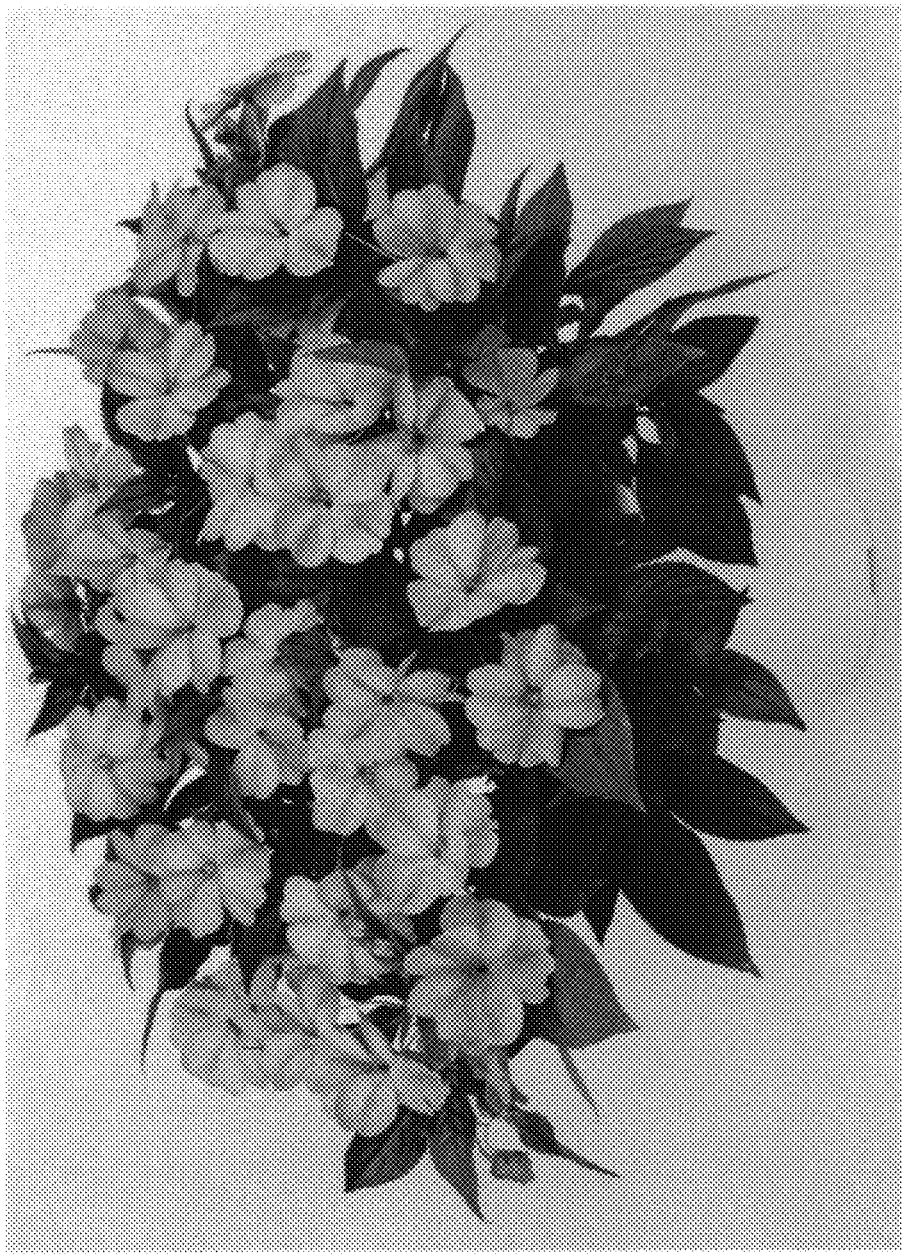

Latin name of the genus and species: *Impatiens hawkeri.*
Variety denomination: 'DIMPSHABO'.

BACKGROUND OF THE INVENTION

The new *Impatiens* cultivar is a product of a planned breeding program conducted by the inventor, Gavriel Danziger in Moshav Mishmar Hashiva, Israel. The objective of the breeding program was to produce new *Impatiens* varieties. The crossing resulting in this new variety was made during September of 2013.

The seed parent is the unpatented, propriety variety referred to as *Impatiens* '2809'. The pollen parent is the unpatented, propriety variety referred to as *Impatiens* '3881'. The new variety was discovered in February 2014 by the inventor in a group of seedlings resulting from the crossing, in a greenhouse in Moshav Mishmar Hashiva, Israel. Date of first sale was Oct. 7, 2018, occurring in the United States. This sale was made directly by the inventor or one who obtained the claimed invention directly or indirectly from the inventor. This sale and all public disclosures made between Oct. 7, 2018 and the filing of this application fall within the exception allowed under 102(b)(1).

Asexual reproduction of the new cultivar 'DIMPSHABO' first by vegetative cuttings was first performed during February 2014, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DIMPSHABO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DIMPSHABO' These characteristics in combination distinguish 'DIMPSHABO' as a new and distinct *Impatiens* cultivar:

1. Large flowers.
2. Unique flower color of violet flushed with purple.
3. Well branched.
4. Sun resistant.

PARENT COMPARISONS

Plants of the new cultivar 'DIMPSHABO' are similar to plants of the seed parent in most horticultural characteristics, however, plants of the new cultivar 'DIMPSHABO' differ in the following;

1. The new variety has larger flowers than the seed parent variety.
2. The new variety has bi-colored flowers, while the seed parent has purple flowers.
3. The new variety has darker foliage than the seed parent variety.

Plants of the new cultivar 'DIMPSHABO' are similar to plants of the pollen parent in most horticultural characteristics, however, plants of the new cultivar 'DIMPSHABO' differ in the following;

1. The new variety is more vigorous, while the pollen parent is more compact.
2. The new variety has smaller leaves than the pollen parent.
3. The new variety has a darker flower color than the pollen parent variety.

COMMERCIAL COMPARISONS

Plants of the new cultivar 'DIMPSHABO' can be compared to the commercial variety *Impatiens* 'DHARSCLVDR', U.S. Plant Pat. No. 27,673. These varieties are similar in most horticultural characteristics; however, 'DIMPSHABO' differs in the following:

1. The new variety has a more vigorous growth habit than this comparator.
2. The new variety has bi-colored flowers, while this comparator has lavender flowers.
3. The new variety has darker foliage than this comparator.

Plants of the new cultivar 'DIMPSHABO' can also be compared to the commercial variety *Impatiens* 'DHAR329', U.S. Plant Pat. No. 24,789. These varieties are similar in most horticultural characteristics; however, 'DIMPSHABO' differs in the following:

1. The new variety has a more vigorous growth habit than this comparator.
2. The new variety has bi-colored flowers, while this comparator has violet flowers.
3. The new variety has darker foliage than this comparator.

BRIEF DESCRIPTION OF THE PHOTOGRAPHS

The accompanying photograph in FIG. 1 illustrates in full color a typical plant of 'DIMPSHABO' grown in a greenhouse, in Moshav Mishmar Hashiva, Israel.

Figure 2:
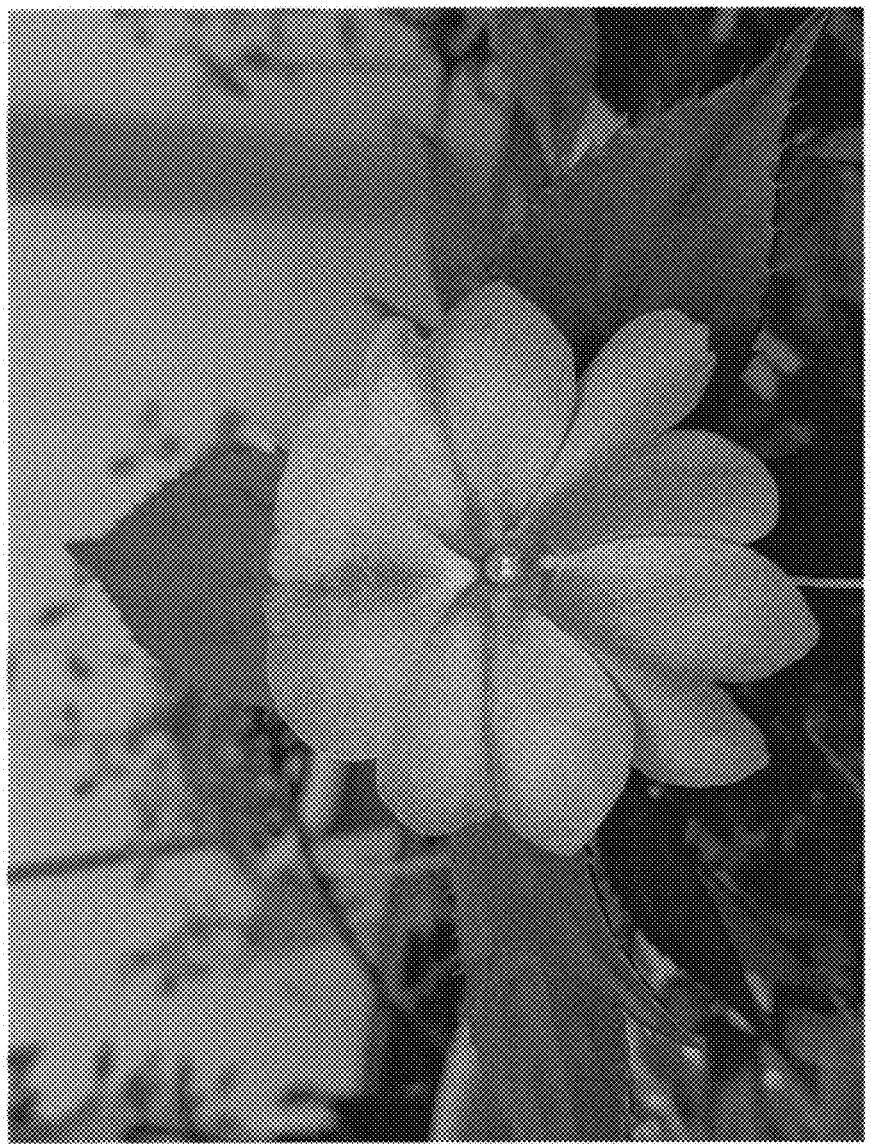

FIG. 2 illustrates in full color a typical inflorescence of 'DIMPSHABO'. Age of the plant photographed is approximately 13 weeks old in a 16 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DIMPSHABO' plants grown in a nursery in Moshav Mishmar Hashiva, Israel, under natural lighting. Measurements were taken during April 2019. The plants were approximately 100 days old in a 16 cm pot. The growing temperature ranged from 20° C. to 35° C. during the days, 15° C. to 25° C. during the nights. Measurements and numerical values represent averages of typical plant types.

Botanical classification: *Impatiens hawkeri* 'DIMPSHABO'.

PROPAGATION

Time to initiate roots: Summer: 10-12 days at 25° C. Winter: 14-20 days at 18° C.

PLANT

Growth habit: Mounded.
Pot size of plant described: 16 cm.
Height: 25 cm.
Plant spread: 45 cm.
Growth rate: Vigorous.
Branching characteristics: Highly branched.
Length of primary lateral branches: 23 cm.
Quantity of primary lateral branches: Average 5-7.
Characteristics of primary lateral branches:
*Form.*—Oval.
*Diameter.*—1 cm.
*Color.*—RHS Greyed-Purple 184A.
*Texture.*—Smooth.
*Strength.*—Strong, very stable.
Internode length: 4 cm.
Root description: Fibrous adventitious roots.

FOLIAGE

Leaf:
*Arrangement.*—Alternate.
*Quantity.*—Approximately 20-25 per branch.
*Average length.*—9 cm.
*Average width.*—4 cm.
*Shape of blade.*—Lanceolate to ovate.
*Apex.*—Attenuate.
*Base.*—Acuminate.
*Margin.*—Ciliate.
*Texture.*—Smooth.
*Pubescence.*—None.
*Aspect.*—45°.
*Color.*—Young foliage upper side: RHS Green N137A. Young foliage under side: RHS Greyed-Red 178A. Mature foliage upper side: RHS Yellow-Green 147A. Mature foliage under side: RHS Greyed-Purple 184B.
*Venation.*—Type: Pinnate. Venation Color: Upper side: RHS Greyed-Purple 184C. Under side: RHS Greyed-Purple 184D.
*Petiole.*—Length: 1.5 cm. Diameter: 0.5 cm. Color: RHS Greyed Purple Group 185C. Texture: Smooth.

FLOWER

Natural flowering season: Flowers at any day length. All year round in a greenhouse environment. Flowering is continuous from spring until fall in an outdoor garden.
Days to flowering from rooted cutting: 10 weeks.
Inflorescence and flower type and habit: Single flowers raised above the foliage. The corolla consists of five petals.
Rate of flower opening: 10-15 days from bud to fully opened flower.
Flower longevity on plant: 5-8 days.
Persistent or self-cleaning: Self-cleaning.
Bud:
*Shape.*—Ovate.
*Length.*—1.5 cm.
*Diameter.*—1 cm.
*Color.*—Near RHS Purple 77B.
Flower size:
*Diameter.*—Average 6.5-7 cm.
*Length.*—0 cm.
Petals:
*Quantity of petals.*—5.
*Arrangement.*—Overlapping.
*Petal length.*—3-3.5 cm.
*Petal width.*—3.5 cm.
*Petal shape.*—Obcordate.
*Apex.*—Heart-shaped.
*Base.*—Acute.
*Margin.*—Entire.
*Texture, upper and lower surface.*—Smooth.

Petal color:

*When opening.*—Upper surface: RHS Violet 84B flushed with Purple N78A. Lower surface: RHS Violet 84B flushed with Purple N78A.

*Fully opened.*—Upper surface: RHS Violet 84B flushed with Red-Purple 72B. Lower surface: RHS Violet 84B flushed with White NN155A.

Spurs:

*Quantity per flower.*—1.

*Length.*—5 cm.

*Diameter.*—0.1 cm.

*Aspect.*—Spur curvature 40°-45° from peduncle.

*Color.*—Towards base: RHS White N155C. Apex: RHS Greyed-Green 196D.

Sepals:

*Quantity per flower.*—2.

*Shape.*—Oblong.

*Length.*—1 cm.

*Width.*—0.5 cm.

*Apex.*—Acute.

*Base.*—Rounded.

*Margin.*—Entire.

*Color.*—RHS Green 142C.

Peduncle:

*Length.*—4.5 cm.

*Diameter.*—0.2 cm.

*Color.*—RHS Green 142C.

*Angle.*—45° to the lateral branch.

*Texture.*—Smooth.

*Strength.*—Stable, flexible.

Fragrance: None.

REPRODUCTIVE ORGANS

Stamens: There are five stamens with introrse anthers that are more or less fused and form a cap over the ovary.

*Number.*—5.

Anthers:

*Shape.*—Oblong.

*Length.*—Approximately 0.4 cm.

*Color.*—RHS Red 178A.

*Pollen.*—Color: RHS White 155D. Quantity: Scant.

Pistil:

*Number.*—1.

*Length.*—0.5 cm.

*Style.*—Length: 0.5 cm. Color: RHS Yellow-Green 144A.

*Stigma.*—Shape: Round. Color: RHS White N155B. Ovary: Color: RHS Yellow-Green 144D.

OTHER CHARACTERISTICS

Seeds and fruits: 5-10 seeds per fruit. Minute, dust-like, brown-grey in color. Color not accurately measured with RHS chart due to size.

Disease/pest resistance, tolerance or susceptibility: None.

Temperature tolerance: Tolerates temperatures from approximately 10° C. to at least 32° C. Uppermost temperature tolerance not observed.

What is claimed is:

1. A new and distinct cultivar of *Impatiens* plant named 'DIMPSHABO' as herein illustrated and described.

* * * * *